United States Patent
Byun et al.

(10) Patent No.: US 12,182,999 B2
(45) Date of Patent: *Dec. 31, 2024

(54) ARTIFICIAL INTELLIGENCE-BASED COLONOSCOPIC IMAGE DIAGNOSIS ASSISTING SYSTEM AND METHOD

(71) Applicant: INFINITT HEALTHCARE CO., LTD., Seoul (KR)

(72) Inventors: Sohyun Byun, Seoul (KR); Chung Il Ahn, Seoul (KR)

(73) Assignee: INFINITT HEALTHCARE CO., LTD., Seoul (KR)

(*) Notice: Subject to any disclaimer, the term of this patent is extended or adjusted under 35 U.S.C. 154(b) by 275 days.

This patent is subject to a terminal disclaimer.

(21) Appl. No.: 17/697,302

(22) Filed: Mar. 17, 2022

(65) Prior Publication Data

US 2022/0301159 A1    Sep. 22, 2022

(30) Foreign Application Priority Data

Mar. 19, 2021  (KR) ........................ 10-2021-0035619

(51) Int. Cl.
*G06T 7/00*    (2017.01)
*A61B 1/00*   (2006.01)
(Continued)

(52) U.S. Cl.
CPC .......... *G06T 7/0012* (2013.01); *A61B 1/0005* (2013.01); *A61B 1/31* (2013.01);
(Continued)

(58) Field of Classification Search
CPC ..................... G06T 7/0012; G06T 7/70; G06T 2207/10016; G06T 2207/10068;
(Continued)

(56) References Cited

U.S. PATENT DOCUMENTS 9,514,416 B2    12/2016  Lee et al.
2013/0195339 A1*  8/2013  Endo ........................ G06T 7/11
                                                        382/131
(Continued)

FOREIGN PATENT DOCUMENTS

KR    10-2011-0042277 A    4/2011
KR       10-1230871 B1     2/2013
(Continued)

OTHER PUBLICATIONS

Corley et al., "Adenoma Detection Rate and Risk of Colorectal Cancer and Death," N Engl J Med 2014, 370, 1298-306.
(Continued)

*Primary Examiner* — Ming Y Hon
(74) *Attorney, Agent, or Firm* — United One Law Group LLC; Kongsik Kim; Jhongwoo Peck

(57) ABSTRACT

A system and method for assisting colonoscopic image diagnosis based on artificial intelligence include a processor, which is configured to analyze each video frame of a colonoscopic image using at least one medical image analysis algorithm and detects a finding suspected of being a lesion in the video frame. The processor calculates the coordinates of the location of the finding suspected of being a lesion. The processor generates display information, including whether the finding suspected of being a lesion is present and the coordinates of the location of the finding suspected of being a lesion.

6 Claims, 7 Drawing Sheets

(51) Int. Cl.
  *A61B 1/31* (2006.01)
  *G06T 7/70* (2017.01)
(52) U.S. Cl.
  CPC ...... *G06T 7/70* (2017.01); *G06T 2207/10016* (2013.01); *G06T 2207/10068* (2013.01); *G06T 2207/20084* (2013.01); *G06T 2207/30028* (2013.01); *G06T 2207/30096* (2013.01)
(58) Field of Classification Search
  CPC . G06T 2207/20084; G06T 2207/30028; G06T 2207/30096; G06T 7/0014; G06T 7/75; G06T 2207/20076; G06T 2207/20081; A61B 1/0005; A61B 1/31
  See application file for complete search history.

(56) References Cited

U.S. PATENT DOCUMENTS

| | | | | |
|---|---|---|---|---|
| 2014/0101080 | A1* | 4/2014 | Lee | G16H 30/40 706/12 |
| 2014/0161327 | A1* | 6/2014 | Motomura | G06T 7/0014 382/128 |
| 2018/0253839 | A1 | 9/2018 | Zur | |
| 2019/0388160 | A1* | 12/2019 | Wood | G01J 3/0229 |
| 2020/0046214 | A1* | 2/2020 | Averbuch | G06T 7/74 |
| 2021/0022586 | A1* | 1/2021 | Mori | A61B 1/045 |
| 2021/0134442 | A1 | 5/2021 | Ahn | |
| 2021/0169306 | A1* | 6/2021 | Oosake | A61B 1/00042 |
| 2021/0406591 | A1* | 12/2021 | Luo | G06T 11/00 |
| 2022/0031227 | A1* | 2/2022 | Cho | G06V 10/82 |
| 2022/0180520 | A1* | 6/2022 | Shang | G06T 7/248 |
| 2022/0189015 | A1* | 6/2022 | Wang | G06V 10/806 |
| 2022/0254017 | A1* | 8/2022 | Rivlin | A61B 1/000096 |
| 2023/0230364 | A1* | 7/2023 | Saikou | G06T 7/0012 382/128 |

FOREIGN PATENT DOCUMENTS

| | | |
|---|---|---|
| KR | 10-1850385 B1 | 5/2018 |
| KR | 10-1938992 B1 | 1/2019 |
| KR | 10-2185886 B1 | 12/2020 |
| WO | 2018/015414 A1 | 1/2018 |

OTHER PUBLICATIONS

Kumar et al., "Adenoma miss rates associated with a 3-minute versus 6-minute colonoscopy withdrawal time: a prospective, randomized trial," Gastrointestinal Endoscopy, 2017.

* cited by examiner

ARTIFICIAL INTELLIGENCE-BASED COLONOSCOPIC IMAGE DIAGNOSIS ASSISTING SYSTEM AND METHOD

CROSS-REFERENCE TO RELATED APPLICATION

This application claims priority from Korean Application No. 10-2021-0035619 filed on Mar. 19, 2021, which is incorporated herein by reference in its entirety.

TECHNICAL FIELD

The present invention relates to a medical image diagnosis assisting apparatus and method using an automated system. More particularly, the present invention relates to an apparatus, system, and method for assisting the diagnosis of a colonoscopic image during colonoscopy by using an artificial intelligence-based medical image analysis algorithm and also assisting the reduction of the risk of missing lesions.

The present invention was derived from the research conducted as part of the SW Computing Industry Fundamental Technology Development Project sponsored by the Korean Ministry of Science and ICT and the Institute of Information & Communications Technology Planning & Evaluation [Project Serial No.: 1711116343; Project No.: 2018-0-00861-003; and Project Name: Intelligent SW Technology Development for Medical Data Analysis].

BACKGROUND ART

Endoscopic diagnosis is a medical practice that is considerably frequently performed for the purpose of regular medical examination. There is a demand for a technology that processes real-time images upon endoscopic diagnosis to preprocess them so that an expert can easily identify a lesion at a medical site. Recently, U.S. Patent Application Publication No. US 2018/0253839 entitled "A System and Method for Detection of Suspicious Tissue Regions in an Endoscopic Procedure" introduced a technology that performed a preprocessing process of removing noise from an image frame and performed a noise removal preprocessing process and a computer-aided diagnosis (CAD) process in parallel, thereby providing real-time diagnosis assistance display information.

In this technology, the accuracy and reliability of a CAD module are recognized as significantly important factors.

Technologies for segmenting or detecting objects in an image or classifying objects in an image are used for various purposes in image processing. In a medical image, objects in the image are segmented, detected, and classified based on the brightness or intensity values of the image, in which case each of the objects may be an organ of the human body, or a lesion.

Recently, the introduction of deep learning and a convolutional neural network (CNN) as artificial neural networks into the automation of an image processing process has dramatically improved the performance of an automated image processing process.

However, on the other hand, the insides of recent artificial neural networks, such as deep learning and a CNN, approximate black boxes, and thus there is reluctance for a user to fully accept and adopt them even when acquired results are excellent. In particular, reluctance to artificial neural networks stands out as being more important in the medical imaging field in which human life is dealt with.

Under this background, research into explainable artificial intelligence (X-AI) has been attempted in the Defense Advanced Research and Planning (DARPA) of the U.S., etc. (see https://www.darpa.mil/program/explainable-artificial-intellig-ence). However, no visible results have yet been revealed.

In the medical field, as a technique for segmenting, detecting, classifying and diagnosing lesions having complex shapes, a technique for selectively applying a plurality of segmentation algorithms is disclosed in International Publication No. WO2018/015414 entitled "Method and System for Artificial Intelligence Based Medical Image Segmentation."

In the related art document, a technique of comparing pre-trained segmentation algorithms and selecting at least one of the pre-trained segmentation algorithms is applied to the acquisition of a final result of image segmentation.

However, descriptive information (explanation) about the criteria for the selective application of the segmentation algorithms cannot be derived from the related art document, and thus a problem arises in that it is difficult to increase a clinician's confidence in the clinical usefulness of this segmentation technique.

Moreover, Korean Patent No. 10-1938992 entitled "CAD System and Method for Generating Description of Reason for Diagnosis" introduced a technology that generated feature vectors by concatenating feature information extracted based on a DNN in order to derive ground information for the diagnosis of a lesion. However, in Korean Patent No. 10-1938992, an artificial neural network derives feature information by itself, and no verification is made as to whether or not the extracted feature information is clinically useful information. Accordingly, there is little evidence that humans can recognize the above information as a description of the diagnosis result of artificial neural networks.

A similar problem is still present in a medical image diagnosis process in that it is difficult to have clinical confidence in a process in which an artificial intelligence diagnosis system that operates like a black box generates a result.

In particular, colonoscopy refers to an examination in which an endoscope is inserted into the human body through the anus and the inside of the colon and the distal end of the small intestine adjacent to the colon are observed. There is a video camera inside the device, so that an operator (a doctor) can detect a polyp and/or abnormal tissue and remove the detected polyp and/or lesion to perform a biopsy or eliminate the polyp and/or tissue while monitoring the inside of the colon with the camera installed in a tube. However, the early detection of polyps is considerably important because polyps can develop into cancer later if they are overlooked during an examination.

During colonoscopy, lesions are often overlooked in the course of examination in a narrow path due to causes such as the resolution of an image, a view in which a user does not intuitively perceive a three-dimensional effect, a blind spot, user error, or the like. In particular, in group health checkups, doctors often exhibit signs of fatigue due to continuous and repetitive procedures, so that lesions may not be sufficiently detected. Therefore, human error may be combined with the cause in terms of the characteristics of images and cause the mission of lesions, which may negatively affect the medical results of examinations.

SUMMARY

Recently, efforts have been made to improve the performance of image segmentation, object detection, and object classification techniques by applying deep learning-based artificial intelligence techniques. However, in the case of deep learning-based artificial intelligence, the fact that there is a black box that prevents a user from determining whether or not a result provided from an operation accidentally exhibits high performance and whether or not a determination process appropriate for a corresponding task has been performed limits the applicability of the deep learning-based artificial intelligence.

In contrast, the use of rule-based training or learning, which is easy to explain, is limited in that better performance cannot be achieved than deep learning. Accordingly, research into deep learning-based artificial intelligence that can provide descriptive information (explanation) while having improved performance is being actively conducted. In the practical application of image processing using an artificial neural network, descriptive information about the basis of diagnosis and classification is required particularly in the medical imaging field. However, descriptive information cannot be derived from the related art.

Even in the above-described related art document (International Publication No. WO2018/015414), it is not possible to derive descriptive information (explanation) on factors that affect the improvement of final segmentation performance, and there is no way to verify that clinically significant feedback has been actually and appropriately applied to the deep learning system even when a clinician provides the clinically significant feedback.

An object of the present invention is to provide evaluation scores, including confidence and accuracy scores, for a plurality of medical image diagnosis algorithms in a process in which a user diagnoses a medical image, thereby improving the accuracy of a medical image diagnosis result obtained by the user.

An object of the present invention is to provide recommended information as descriptive information in a process in which a user derives a final diagnosis result by using artificial intelligence medical image diagnosis algorithms, and to allow the user to provide information about the clinical usefulness of the medical image diagnosis algorithms as quantified information.

An object of the present invention is to generate and provide an optimized combination of a plurality of artificial intelligence medical image diagnosis results as display information for each real-time image frame.

An object of the present invention is to provide an optimized combination of a plurality of artificial intelligence medical image diagnosis results capable of efficiently displaying diagnosis results that are likely to be acquired, are likely to be overlooked, or have a high level of risk in a current image frame.

An object of the present invention is to provide a user interface and diagnosis computing system that automatically detect and present diagnosis results that are likely to be acquired, are likely to be overlooked, or have a high level of risk in a current image frame, so that medical staff can check and review the diagnosis results in real time during an endoscopy.

An object of the present invention is to train on polyps, etc., which may be missed by a user, based on artificial intelligence medical image diagnosis results for each real-time video frame of a colonoscopic image via an artificial intelligence algorithm and then apply the results of the training to an artificial intelligence diagnosis assisting system, thereby increasing work efficiency and diagnostic accuracy.

In general, it is known that an increase in the early detection rate of polyps has a close correlation with a decrease in the incidence of cancer. Accordingly, an object of the present invention is to reduce the incidence of colorectal cancer by increasing lesion detection rate and also eliminating colorectal cancer risk factors in their early stages. Furthermore, an object of the present invention is to contribute to reducing the causes of colorectal cancer and also reducing the frequency of examinations by enabling doctors to find and treat more lesions than before. The present invention utilizes polyps having various sizes and/or shapes, found and verified in real situations, together with the locations at which they are found as training data for artificial intelligence/an artificial neural network. An object of the present invention is to increase polyp finding/detection rate by automatically finding a polyp having a considerably small size, which is easy to overlook with the human eye, and a polyp located in a blind spot by using the artificial intelligence/artificial neural network trained using the above training data and also to lower the risk of developing colon cancer via the above increase in polyp finding/detection rate.

An object of the present invention is to automatically detect a polyp/lesion that may easily be missed by a user during colonoscopy and present the location of the polyp/lesion in a colorectal path (a colonoscopic/colonoscopy path), so that the user may easily check the polyp/lesion in real time during colonoscopy and even a report adapted to enable other examiners to check it later may be generated through a simple operation.

In a diagnosis assisting technology for colonoscopic images, which is an application target of the present invention, when polyps and/or lesions having various sizes, shapes and locations are located together with the colon wall or folds in the colon, it is easy to miss polyps and/or lesions when the polyps and/or lesions are not different in color from surrounding tissues and have small sizes. Accordingly, an object of the present invention is to provide a method that may further improve polyp detection rate in the colon by detecting various lesions in real time via artificial intelligence and also to help other examiners to check polyp candidates again later by providing the locations of the polyps in a colonoscopic/colonoscopy path.

According to an aspect of the present invention, there is provided a colonoscopic image diagnosis assisting system including a computing system, wherein the computing system includes a receiving interface; memory or a database; a processor; and a user display. The receiving interface is configured to receive a medical image (a colonoscopic image) as the medical image, and the memory or a database is configured to store at least one medical image analysis algorithm having a function of analyzing the medical image (the colonoscopic image).

The processor is configured to analyze each video frame of the colonoscopic image using the at least one medical image analysis algorithm, and to detect a finding suspected of being a lesion in the video frame; the processor is further configured to calculate the coordinates of the location of the finding suspected of being a lesion; and the processor is further configured to generate display information, including whether the finding suspected of being a lesion is present and the coordinates of the location of the finding suspected of being a lesion.

The user display is configured to display the finding suspected of being a lesion so that it is visually distinguished in the video frame based on the display information and display the coordinates of the location of the finding suspected of being a lesion so that they are visually associated with the finding suspected of being a lesion.

The processor may be further configured to calculate the location of the finding suspected of being a lesion in a colonoscopic path; and the processor may be further configured to generate display information, including whether the finding suspected of being a lesion is present, the coordinates of the location of the finding suspected of being a lesion, and the location of the finding suspected of being a lesion in the colonoscopic path.

The user display may be further configured to display the location of the finding suspected of being a lesion in the colonoscopic path so that it is visually associated with the finding suspected of being a lesion based on the display information.

The processor may be further configured to track the location of the video frame, indicative of a current examination region, in the colonoscopic path; and the processor may be further configured to calculate the location of the finding suspected of being a lesion in the colonoscopic path based on the location of the video frame in the colonoscopic path and the coordinates of the location of the finding suspected of being a lesion.

The processor may be further configured to calculate the location of the finding suspected of being a lesion in the colonoscopic path based on a pre-examination medical image including the three-dimensional anatomical structure of a patient to be examined.

The artificial intelligence-based medical image (colonoscopic image) analysis algorithm may be trained using a label, including an indication of a lesion detected for each video frame, the coordinates of the location of the lesion in the video frame, and the location of the lesion in a colonoscopic path, together with each video frame as training data. Accordingly, the processor may calculate the location of the finding suspected of being a lesion in the video frame in the colonoscopic path by using the medical image analysis algorithm.

The processor may be further configured to extract context-based diagnosis requirements corresponding to the characteristics of the video frame in the medical image by analyzing the video frame of the medical image. The processor may be further configured to select a diagnosis application algorithm to perform diagnosis on the video frame from among a plurality of diagnosis application algorithm candidates based on the context-based diagnosis requirements.

In an embodiment of the present invention, the receiving interface may be further configured to receive at least one colonoscopic image from at least one colonoscopic image acquisition module. In this case, the processor may be further configured to detect a finding suspected of being a lesion for each video frame of the at least one colonoscopic image by using the at least one medical image analysis algorithm. The processor may be further configured to generate display information, including whether the finding suspected of being a lesion is present and the coordinates of the location of the finding suspected of being a lesion, for each video frame of the at least one colonoscopic image.

According to another aspect of the present invention, there is provided a colonoscopic image diagnosis assisting method that is performed by a colonoscopic image diagnosis assisting system including a processor and a user display and utilizes at least one medical image analysis algorithm having a function of analyzing a colonoscopic image stored in memory or a database inside the colonoscopic image diagnosis assisting system.

The colonoscopic image diagnosis assisting method includes: receiving a colonoscopic image; analyzing, by the processor, each video frame of the colonoscopic image by using at least one medical image analysis algorithm, and detecting, by the processor, a finding suspected of being a lesion in the video frame; when the finding suspected of being a lesion is present in the video frame, calculating, by the processor, the coordinates of the location of the finding suspected of being a lesion; generating, by the processor, display information, including whether the finding suspected of being a lesion is present and the coordinates of the location of the finding suspected of being a lesion; and, when the finding suspected of being a lesion is present in the video frame, displaying, by the user display, the finding suspected of being a lesion so that it is visually distinguished in the video frame based on the display information; and displaying, by the user display, the coordinates of the location of the finding suspected of being a lesion so that they are visually associated with the finding suspected of being a lesion.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
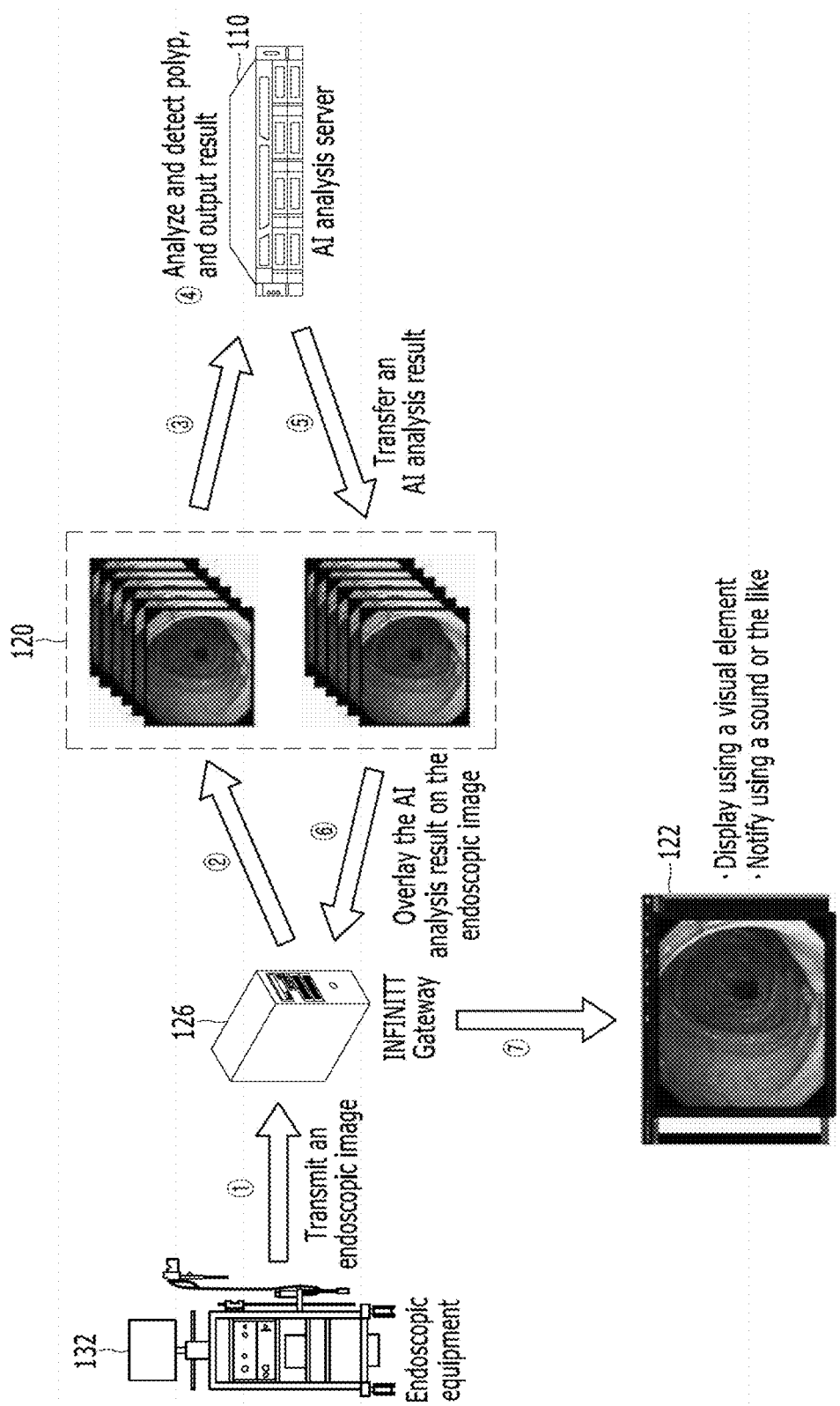
FIG. 1 is a view showing an artificial intelligence-based colonoscopic image diagnosis assisting system according to an embodiment of the present invention and a workflow using the same.

Other objects and features of the present invention in addition to the above-described objects will be apparent from the following description of embodiments to be given with reference to the accompanying drawings.

Embodiments of the present invention will be described in detail below with reference to the accompanying drawings. In the following description, when it is determined that a detailed description of a known component or function may unnecessarily make the gist of the present invention obscure, it will be omitted.

When recently rapidly developed deep learning/CNN-based artificial neural network technology is applied to the imaging field, it may be used to identify visual elements that are difficult to identify with the unaided human eye. The application of this technology is expected to expand to various fields such as security, medical imaging, and non-destructive inspection.

For example, in the medical imaging field, there are cases where cancer tissue is not immediately diagnosed as cancer during a biopsy but is diagnosed as cancer after being tracked and monitored from a pathological point of view. Although it is difficult for the human eye to confirm whether or not corresponding cells are cancer in a medical image, there is an expectation that the artificial neural network technology can provide a more accurate prediction than the human eye.

However, although the artificial neural network technology can yield better prediction/classification/diagnosis results than the human eye in some studies, there is a lack of descriptive information about prediction/classification/diagnosis results acquired through the application of the artificial neural network technology, and thus a problem arises in that it is difficult to accept and adopt the above results in the medical field.

The present invention has been conceived from the intention to improve the performance of the classifying/predicting objects in an image, which are difficult to classify with the unaided human eye, through the application of the artificial neural network technology. Furthermore, even in order to improve the classification/prediction performance of the artificial neural network technology, it is significantly important to acquire descriptive information about the internal operation that reaches the generation of a final diagnosis result based on the classification/prediction processes of the artificial neural network technology.

The present invention may present the performance indicators and clinical usefulness of a plurality of medical image diagnosis algorithms based on artificial neural networks as quantified indicators. As a result, it is possible to provide descriptive information about a process of acquiring a final diagnosis result based on the classification/prediction processes of the artificial neural network, and it is also possible to provide a reference for the determination of whether or not a human user can adopt the classification/prediction/diagnosis results of an artificial neural network.

When the artificial neural networks of the related arts are applied to the diagnosis of medical images, they are overfitted only for given tasks, so that statistical accuracy is high but accuracy is low in some clinically important diagnostic points. Many neural networks of the related art are in such a situation, and thus there occur frequent cases where it is difficult for clinicians to have confidence in the diagnosis results for medical images to which the artificial neural networks are applied. This risk is more obvious in that IBM's Watson Solution, a well-known artificial neural network, exhibits a problem in that it is overfitted for patient race information included in learned data and thus it is significantly low in accuracy in the case of the dataset of new race patients.

Therefore, it is significantly important to provide a route through which quantified indicators regarding whether or not clinicians will accept these diagnosis results can be provided and clinicians can provide direct feedback on the generation of the quantified indicators while maximally utilizing the excellent analytical/diagnostic potential of the artificial neural networks.

The aforementioned U.S. Patent Application Publication No. US 2018/0253839 entitled "A System and Method for Detection of Suspicious Tissue Regions in an Endoscopic Procedure," International Publication No. WO2018/015414 entitled "Method and System for Artificial Intelligence Based Medical Image Segmentation," and Korean Patent No. 10-1938992 entitled "CAD System and Method for Generating Description of Reason for Diagnosis" disclose basic components for the artificial intelligent-based diagnosis of endoscopic images, i.e., an endoscopic image acquisition module, an image capture and image processing module, and a transmission/reception interface (module) which transmits an acquired/captured endoscopic image to a computing system equipped with an analysis engine, and memory or a database in which an artificial intelligence/artificial neural network-based image analysis algorithm/engine is stored.

In the present invention, a data storage means, a computation means, the basic concept and structure of an artificial neural network, a transmission/reception interface for transferring input data (an image), etc. are required to implement an invention. However, detailed descriptions of these basic elements may make the gist of the present invention obscure. Among the components of the present invention, the items known to those of ordinary skill in the art prior to the filing of the present application will be described as parts of the components of the present invention in the present specification, if necessary. However, if it is determined that a fact obvious to those of ordinary skill in the art may make the gist of the invention obscure, a description thereof may be omitted.

In addition, descriptions of the items omitted therein may be replaced by providing notification that the items are known to those of ordinary skill in the art via the related art documents, e.g., U.S. Patent Application Publication No. US 2018/0253839 entitled "A System and Method for Detection of Suspicious Tissue Regions in an Endoscopic Procedure," International Publication No. WO2018/015414 entitled "Method and System for Artificial Intelligence Based Medical Image Segmentation," and Korean Patent No. 10-1938992 entitled "CAD System and Method for Generating Description of Reason for Diagnosis," that are cited therein.

A medical image diagnosis assisting apparatus and method according to embodiments of the present invention will be described in detail below with reference to FIGS. 1 to 7.

FIG. 1 is a view showing an artificial intelligence-based colonoscopic image diagnosis assisting system according to an embodiment of the present invention and a workflow using the same.

Figure 2:
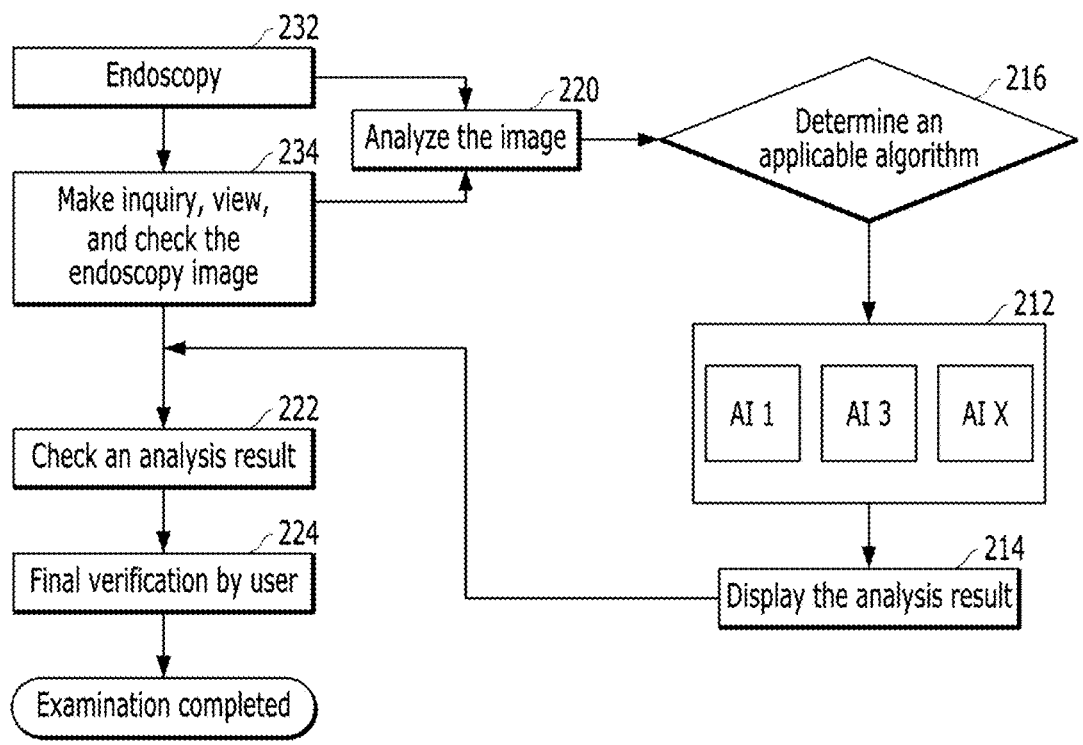
FIG. 2 is a view showing the workflow of an artificial intelligence-based colonoscopic image diagnosis assisting system according to an embodiment of the present invention.

FIG. 2 is a view showing the workflow of an artificial intelligence-based colonoscopic image diagnosis assisting system according to an embodiment of the present invention.

Referring to FIGS. 1 and 2 together, the colonoscopic image diagnosis assisting system according to the present embodiment includes a computing system, and the computing system includes a receiving interface; memory or a database; a processor; and a user display.

The colonoscopic image diagnosis assisting system according to the present embodiment may include one computing system, or may include a plurality of computing systems. In this case, the plurality of computing systems may perform individual functions, and may perform the workflow of the colonoscopic image diagnosis assisting system in cooperation with other computing systems.

For example, one of the computing systems may be an artificial intelligence analysis server 110. The artificial intelligence analysis server 110 may analyze and detect whether a polyp is present in each frame by analyzing a medical image (a colonoscopic image), and may generate and output the results of the analysis and detection.

For example, the receiving interface (not shown) of the artificial intelligence analysis server 110 receives a medical image, and the memory or database of the artificial intelligence analysis server 110 may store at least one medical image analysis algorithm 212 having a function of diagnosing a medical image (a colonoscopic image). In this case, referring to FIGS. 1 and 2, the medical image transferred to the artificial intelligence analysis server 110 may be an image set that is the result of image analysis 220 performed by an artificial intelligence workstation 120 and is image-processed and standardized such that it can be compared with training input data.

The colonoscopic image acquisition module 132 may transfer a colonoscopic image, acquired in real time during endoscopy 232, to a gateway 126 in a DICOM format. In this case, not only a real-time image during the endoscopy 232 but also an image of the colonoscopic image acquisition module 132 during the endoscopy 232 may be stored in a database in a hospital. Thereafter, even when the image is inquired, viewed and/or checked by the same user or another user (see 234), the colonoscopic image diagnosis assisting system of the present invention may be applied.

In this case, the colonoscopic image acquisition module 132 may convert a non-DICOM image into a DICOM format and transmit it to the gateway 126. The gateway 126 may convert a DICOM image into a JPEG format and transmit it to the artificial intelligence workstation 120.

In another embodiment of the present invention, the colonoscopic image acquisition module 132 may transfer a colonoscopic image, acquired in real time, to the gateway 126 as a non-DICOM image, and the gateway 126 may convert the non-DICOM image into a DICOM format and transfer a DICOM image or JPEG/MPEG format image to the artificial intelligence workstation 120.

The artificial intelligence workstation 120 may also include a receiving interface (not shown). The processor (not shown) of the artificial intelligence workstation 120 may perform image processing, including cropping adapted to remove the black border portion of a colonoscopic image and/or a captured image, rotation/tilting, and the correction of image brightness values, as part of the image analysis 220. The processor of the artificial intelligence workstation 120 may transfer the medical image, converted into a standardized format as a result of the image analysis 220, to the artificial intelligence analysis server 110. In this case, the standardized format may be a well-known format, such as PNG, JPEG, or MPEG, for the purpose of the easy application of an artificial neural network.

The processor (not shown) of the artificial intelligence analysis server 110 may analyze the video frame of the colonoscopic image (already processed through the image analysis 220) using the at least one medical image analysis algorithm 212, and may detect a finding suspected of being of lesion/colon, whether the finding suspected of being a lesion/colon is present within the video frame. When the finding suspected of being a lesion is present in the video frame, the processor calculates the coordinates of the location of the finding suspected of being a lesion, and generates an analysis result 214 including whether the finding suspected of being a lesion is present and the coordinates of the location of the finding suspected of being a lesion. The processor generates display information to be displayed together with the colonoscopic image based on the analysis result 214.

The processor of the artificial intelligence analysis server 110 may extract context-based diagnosis requirements corresponding to the characteristics of the video frame by analyzing the video frame of the medical image (see 216). In this case, the processor may select at least one diagnosis application algorithm to perform the diagnosis/analysis of the video frame from among the plurality of medical image analysis algorithms 212, i.e., diagnosis application algorithm candidates, based on the context-based diagnosis requirements.

The user display 122 displays the analysis result 214 together with the colonoscopic image so that a user can check it (see 222). In other words, when a finding suspected of being a lesion is present in the video frame, the user display 122 displays the finding suspected of being a lesion so that it can be visually distinguished in the video frame based on the display information, and also displays the coordinates of the location of the finding suspected of being a lesion so that they can be visually associated with the finding suspected of being a lesion. The user's final verification (see 224) process is performed in such a manner that a user (a medical professional) accepts or rejects the finding suspected of being a lesion displayed in the current video frame.

The processor of the artificial intelligence analysis server 110 may calculate the location of the finding suspected of being a lesion in a colonoscopic/colonoscopy path, and may generate display information including whether the finding suspected of being a lesion is present, the coordinates of the location of the finding suspected of being a lesion, and the location of the finding suspected of being a lesion in the colonoscopic path. In this case, the processor may calculate the location of the finding suspected of being a lesion in the colonoscopic path based on the information of a sensor on a colonoscopic device and/or the analysis result 214 of the artificial intelligence algorithm 212.

The user display 122 may display the location of the finding suspected of being a lesion in the colonoscopic path so that it is visually associated with the finding suspected of being a lesion based on the display information (see 222), with the result that a user can check it.

The processor of the artificial intelligent analysis server 110 may track the location of a video frame, indicative of a current examination region, in the colonoscopic path, and may calculate the location of the finding suspected of being a lesion in the colonoscopic path based on the location of the video frame in the colonoscopic path and the coordinates of the location of the finding suspected of being a lesion.

The processor of the artificial intelligent analysis server 110 may calculate the location of the finding suspected of being a lesion in the colonoscopic path based on a pre-examination medical image including the three-dimensional (3D) anatomical structure of a patient to be examined.

The analysis result 214 provided by the artificial intelligence analysis server 110 may include the detected coordinates of the lesion/polyp, the probability that the lesion/polyp is detected, and/or the location of the lesion/polyp in the colonoscopic path.

A user may finally verify the display information displayed together with the endoscopic image (see 224), may accept or reject the finding suspected of being a lesion, included in the display information, as a lesion, and may, when the finding suspected of being a lesion is accepted as a lesion, take subsequent actions for the lesion or prepare a report in order to take subsequent actions later, thereby causing colonoscopy to be terminated.

The artificial intelligence-based medical image (colonoscopic image) analysis algorithm 212 may be trained using a label, including an indication of a lesion detected for each video frame, the coordinates of the location of the lesion in the video frame, and the location of the lesion in a colonoscopic path, together with each video frame as training data. Accordingly, the processor may calculate the location of the finding suspected of being a lesion in the video frame in the colonoscopic path by using the medical image analysis algorithm 212, and may provide it as the analysis result 214.

In an embodiment of the present invention, a main means for identifying a current location in a path indicated by an endoscopic image may mainly depend on learning and inference regarding endoscopic images.

In this case, when a current location in a colonoscopic path is identified depending on learning and reasoning regarding endoscopic images, the label of each endoscopic image used for learning may include information about a location in an endoscopic (colonoscopic) path and information about a lesion detected/verified (an image actually verified through biopsy) separately for each frame.

In another embodiment of the present invention, learning and inference regarding endoscopic images is a main means for identifying a current location in a colorectal path, and additionally a current location may be more accurately identified by combining the main means with an additional means for identifying the current location by estimating the progress speed of frames of an endoscopic image through image analysis.

Furthermore, in general, it is difficult to take a CT image before endoscopy, so that it is necessary to identify a current location in a colorectal path by relying only on an endoscopic image. However, if it is possible to take a CT image before endoscopy, a current location may be identified in association with a 3D model of an endoscopic target (the colon) reconstructed based on a CT image taken before endoscopy in another embodiment of the present invention.

In this case, a CT image-based 3D model of the colon may be implemented in combination with virtual endoscopic imaging technology, which corresponds to the patent issued to the present applicant (Korean Patent No. 10-1850385 or 10-1230871).

Furthermore, according to another embodiment of the present invention, when a current location in an endoscopic path within an endoscopic examination target (the colon) is identified, correction (compensation) may be performed in association with an endoscope or a sensor installed in an endoscopic device (a sensor capable of detecting the length of an endoscope inserted into the human body) rather than relying solely on image analysis.

According to an embodiment of the present invention, the receiving interface of the artificial intelligence analysis server 110 may receive at least one endoscopic image from at least one endoscopic image acquisition module. In this case, the processor of the artificial intelligence analysis server 110 may detect whether a finding suspected of being a lesion is present in each video frame of at least one endoscopic image by using at least one medical image analysis algorithm 212. The processor may generate display information, including information about whether a finding suspected of being a lesion is present and the coordinates of the location of the finding suspected of being a lesion, for each video frame of at least one colonoscopic image.

The display information may include whether a finding suspected of being a lesion is present, the coordinates of the location of the finding suspected of being a lesion (the coordinates of a location within a current video frame), and the location of the finding suspected of being a lesion in a colonoscopic path.

The finding suspected of being a lesion is visualized to be visually distinguished from other parts in the video frame of the colonoscopic image. In this case, the corresponding finding may be marked with a visualization element such as a marker/box, or may be highlighted.

Furthermore, information about the location and the probability that the lesion in question is actually a lesion (the probability inferred by artificial intelligence) are included in the display information so that it can be visualized such that a user can intuitively understand the proximity or relevance of the finding suspected of being a lesion to the visualization element.

The display information may include an endoscopic image frame, a diagnosis result selectively overlaid on the endoscopic image frame, information about a diagnosis application algorithm having generated the diagnosis result, and an evaluation score for the diagnosis application algorithm.

Artificial intelligence diagnosis algorithms may be applied to diagnosis in the descending order of the evaluation score. However, in special situations, weights may be adaptively allocated to the detailed items of the evaluation score.

A medical image diagnosis assisting method according to another embodiment of the present invention is performed by a processor in a diagnosis assisting system (a computing system, e.g., the artificial intelligence analysis server 110) that assists the diagnosis of medical images, and is performed based on program instructions that are loaded into the processor.

A colonoscopic image diagnosis assisting method according to an embodiment of the present invention is performed by the colonoscopic image diagnosis assisting system (a computing system, e.g., the artificial intelligence analysis server 110) including the processor and the user display 122, and may utilize the at least one medical image analysis algorithm 212 having a colonoscopic analysis function stored in the memory or the database included in the colonoscopic image diagnosis assisting system.

The method of the present invention includes the steps of: receiving a colonoscopic image; analyzing, by the processor, each video frame of a colonoscopic image by using the at least one medical image analysis algorithm 212, and detecting, by the processor, whether a finding suspected of being a lesion is present in the video frame; calculating, by the processor, the coordinates of the location of a finding suspected of being a lesion when the finding suspected of being a lesion is present in the video frame; generating, by the processor, display information including whether a finding suspected of being a lesion is present and the coordinates of the location of the finding suspected of being a lesion; when the finding suspected of being a lesion is present in the video frame, displaying, by the user display, the finding suspected of being a lesion on the video frame so that it is visually distinguished in the video frame based on the display information; and displaying, by the user display, the coordinates of the location of the finding suspected of being a lesion so that they are visually associated with the finding suspected of being a lesion.

In this case, the method of the present invention may further include the step of calculating, by the processor, the location of a finding suspected of being a lesion in a colonoscopic path.

In the method of the present invention, the step of generating the display information includes the step of generating, by the processor, display information, including whether a finding suspected of being a lesion, the coordinates of the location of the finding suspected of being a lesion, and the location of the finding suspected of being a lesion in the colonoscopic path.

In the method of the present invention, the step of displaying, by the user display, the coordinates of the location of the finding suspected of being a lesion so that they are visually associated with the finding suspected of being a lesion includes the step of displaying, by the user display, the location of the finding suspected of being a lesion in the colonoscopic path so that it is visually associated with the finding suspected of being a lesion.

In the method of the present invention, the step of receiving the colonoscopic image may include the step of receiving at least one colonoscopic image from the at least one colonoscopic image acquisition module.

In the method of the present invention, the step of detecting whether a finding suspected of being a lesion is present in the video frame includes the step of detecting whether a finding suspected of being a lesion is present in each video frame of the at least one endoscopic image by using the at least one medical image analysis algorithm.

In the method of the present invention, the step of generating the display information includes the step of generating display information, including information about whether a finding suspected of being a lesion is present for each video frame of the at least one endoscopic image and the coordinates of the location of the finding suspected of being a lesion.

Figure 3:
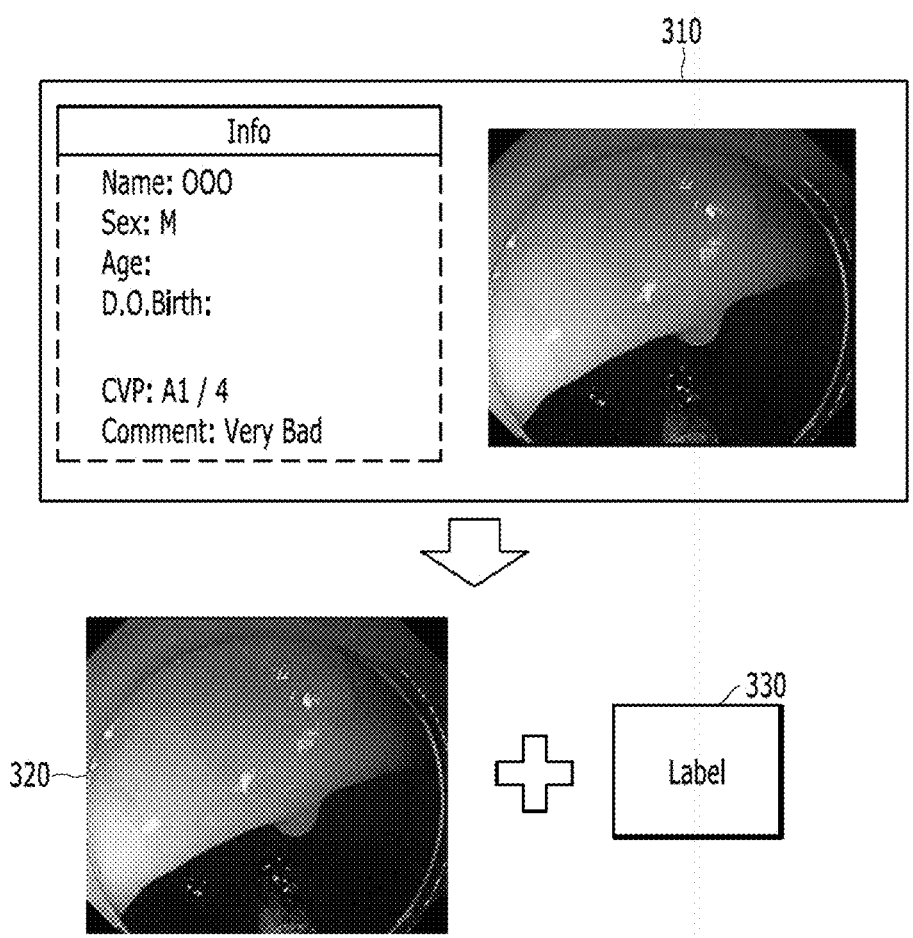
FIG. 3 is a view showing a process of generating training data through the image processing/analysis of a colonoscopic image according to an embodiment of the present invention.

FIG. 3 is a view showing a process of generating training data through the image processing/analysis of a colonoscopic image according to an embodiment of the present invention.

Referring to FIG. 3, there is shown an embodiment of the raw image 310 of a colonoscopic image obtained from a colonoscopy diagnosis apparatus according to an embodiment of the present invention. The raw image 310 of the colonoscopic image includes a colonoscopic image part 320 of an examination region, and display information.

In the process of training an artificial intelligence analysis algorithm for colonoscopic images according to an embodiment of the present invention, training input data includes the following. The raw image 310 of a colonoscopy image used as input data for training includes an image including a black background having a size varying depending on the resolution supported by an image acquisition device (a colonoscopic image acquisition module). In order to use only colonoscopic image information, endoscopic image cropping is performed prior to training. Although the training input data may include the raw image 310, the colonoscopic image part 320 and label information 330 obtained through the cropping are mainly used.

From the raw image 310, information about a patient, clinical requirements for the patient, verified diagnostic comments for a colonoscopic image frame, and a lesion detection result for the colonoscopic image frame are extracted and generated as the label information 330. In this case, the information about the patient and clinical requirements for the patient may be entirely extracted from the raw image 310, or may be supplemented by using in-hospital databases such as PACS, EMR, OCS, CIS, and HIS. In this case, the location in a colonoscopic path corresponding to the frame of the raw image 310 may also be extracted and included in the label information 330.

In a learning (training) stage, a location in a colonoscopic path may be learned along with information for the detection of a lesion (in the state of being included in label information), and, finally, the coordinate values where the lesion is located, the probability of being a lesion, and the result of the location in the path may be learned.

In a process of performing inference for a real-time image after learning, the result value of the analysis is displayed on the user screen by using a visualization element that can be visually distinguished. In this case, a process of extracting features from the colonoscopic image part 320 in the artificial intelligence analysis server 110 or the like may be performed by an artificial neural network-based image analysis process such as ResNet-50. At least one feature for each layer extracted by ResNet-50 is provided to an FPN (feature pyramid network) along with a box probability value, including a class probability value for whether a polyp in question is a polyp for each layer and information about the location of the polyp, it is determined whether the polyp has been accurately detected by calculating the values, learning is performed, and, finally, the result of the coordinate values where the polyp is located are obtained.

In order to further reduce a user's risk of missing, when a dangerous finding is found, the user's attention may be called by using an alarm sound additionally. When the risk of mission is high due to the type of dangerous finding, the probability that the dangerous finding is a lesion, or the location of the dangerous finding in a blind spot in the field of view, different alarm sounds may be used in respective cases in order to further call the user's attention.

As a means for calling the user's attention, a bounding box including a lesion/polyp risk region may be displayed on the user display 122, or a specific message or a lesion/polyp risk region may be displayed via a pop-up window. This alarm sound, bounding box, message, or pop-up window may be maintained for a specific amount of time (e.g., one second).

When training data is generated, the augmentation of data may be performed in order to resolve overfitting attributable to a specific bias (the color, brightness, resolution, or tilting of an endoscope device) of the data. The augmentation of data may be achieved through the rotation/tilting, movement, symmetry, and correction of the color/brightness/resolution of image data.

In addition, as an example of a method for preventing overfitting, there may be used various methods such as the weight regulation, dropout addition, and network capacity adjustment (reduction) of an artificial neural network included in the artificial intelligence analysis server 110.

A process of generating the training data of FIG. 3 may be performed as a part of the image analysis 220 performed by the artificial intelligence workstation 120 of FIG. 1. However, in another embodiment of the present invention, the artificial intelligence analysis server may perform all the functions of the artificial intelligence workstation, and the artificial intelligence analysis server may perform the image analysis 220 and the generation of training data.

Meanwhile, the image analysis/processing process such as cropping performed in the learning stage may be performed as part of the image analysis (220) process even in the inference stage, so that the artificial intelligence analysis server 110 may receive a standardized input image to be compared with training data and apply the artificial neural network and/or the image analysis algorithm 212.

Figure 4:
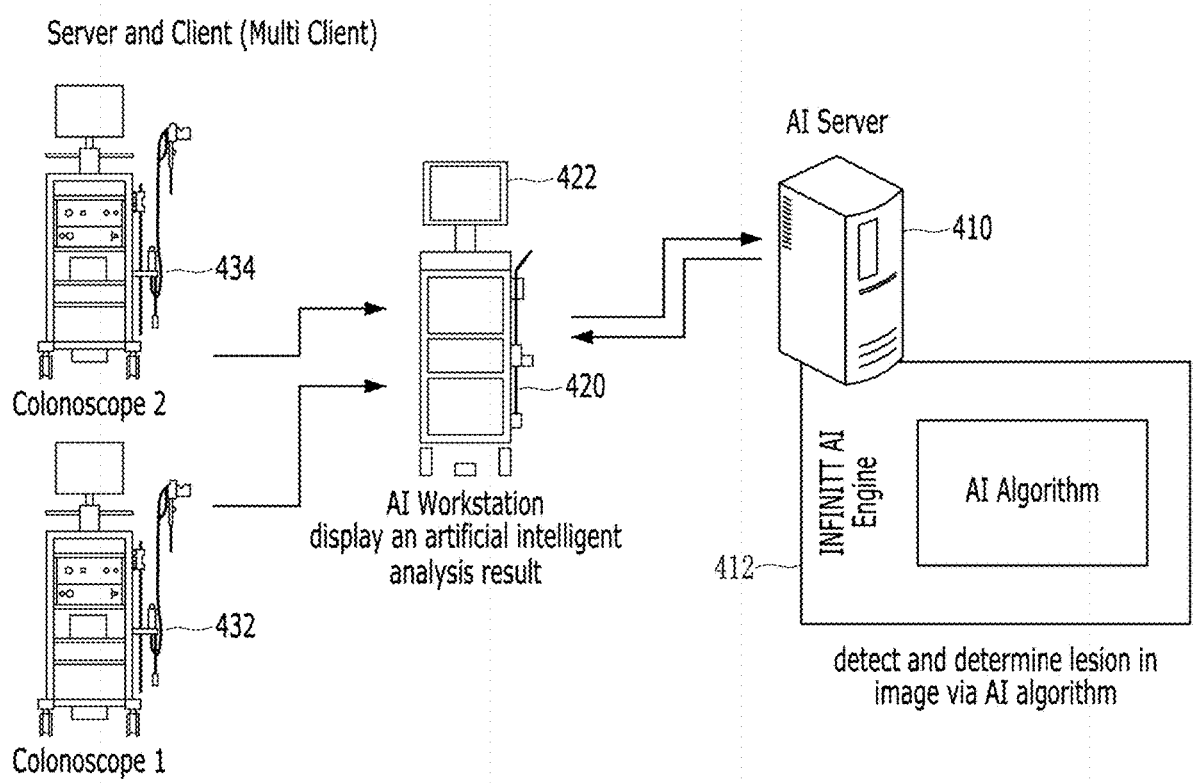
FIG. 4 is a diagram showing a colonoscopic image diagnosis assisting system having a multi-client structure and peripheral devices according to an embodiment of the present invention.

FIG. 4 is a diagram showing a colonoscopic image diagnosis assisting system having a multi-client structure and peripheral devices according to an embodiment of the present invention.

A first colonoscopic image acquisition module 432 may transfer a colonoscopic image, acquired in real time, to an artificial intelligence workstation 420 in real time, or may transfer a captured image of a colonoscopic image to the artificial intelligence workstation 420.

A second colonoscopic image acquisition module 434 may transfer a colonoscopic image, acquired in real time, to the artificial intelligence workstation 420 in real time, or may transfer a captured image of a colonoscopic image to the artificial intelligence workstation 420.

In this case, the artificial intelligence workstation 420 may include an input/reception interface module (not shown) configured to receive a colonoscopic image (or a captured image) received from the first colonoscopic image acquisition module 432 and the second colonoscopic image acquisition module 434.

The artificial intelligence workstation 420 may transfer a video frame of a received/acquired colonoscopic image to an artificial intelligence server 410. In this case, the image transferred to the artificial intelligence server 410 may be transferred in a standardized JPEG or MPEG format. The artificial intelligence server 410 may also include an input/reception interface module (not shown) configured to receive a video frame image in a standardized format.

The artificial intelligence server 410 may detect and determine a lesion in a video frame/image by using an artificial intelligence algorithm (a medical image analysis algorithm) 412.

A processor (not shown) in the artificial intelligence server 410 may input given image data to the artificial intelligence algorithm 412, may receive the analysis result of the artificial intelligence algorithm 412, and may control a data transfer process between memory or storage (not shown) having the artificial intelligence algorithm 412 stored therein and the processor during the above process.

The output interface module (not shown) of the artificial intelligence server 410 may transfer the analysis result of the artificial intelligence algorithm 412 to the artificial intelligence workstation 420. In this case, the transferred information may include whether a finding suspected of being a lesion is detected within a video frame, the coordinates at which the finding suspected of being a lesion is detected, the probability that the finding suspected of being a lesion is a lesion, and the location of the finding suspected of being a lesion in a colorectal or colonoscopic path.

The artificial intelligence workstation 420 may display the analysis result of the artificial intelligence algorithm 412 on a user display 422. In this case, the information displayed on the user display 422 may include whether a finding suspected of being a lesion is detected within a video frame of a currently displayed colonoscopic image, the finding suspected of being a lesion that is visualized to be visually distinguished in the video frame (e.g., the finding suspected of being a lesion that is highlighted, or the finding suspected of being a lesion that is surrounded with a box), the coordinates of the location of the finding suspected of being a lesion within the video frame, and the location of the finding suspected of being a lesion in a colorectal or colonoscopic path.

In this case, a plurality of colonoscopic images may be simultaneously displayed on the user display 422 in real time. Individual colonoscopic image video frames may be displayed for respective windows on a screen.

In real-time examination, when a user immediately detects a finding suspected of being a lesion on a colonoscopic image and takes action, there is no significant problem. In contrast, when a user misses a finding suspected of being a lesion in a real-time examination, it is substantially impossible to re-diagnose the missing finding suspected of being a lesion in the related arts.

Meanwhile, the present invention has advantages in that a captured video frame may be re-checked by other users later, in that even when an endoscope has already advanced, a previous video frame may be recalled and the missing finding suspected of being a lesion may be re-diagnosed, and in that even after endoscopy has been finished, the coordinates of the location of a finding suspected of being a lesion within the video frame and the location of the finding suspected of being a lesion in a colonoscopic path are provided together, and thus the location of the finding suspected of being a lesion may be identified, so that follow-up actions may be taken.

Although FIG. 4 shows an embodiment in which the artificial intelligence workstation 420 and the artificial intelligence server 410 are separated from each other for convenience of description, this is merely an embodiment of the present invention. However, it will be apparent to those of ordinary skill in the art that according to another embodiment of the present invention, the artificial intelligence workstation 420 and the artificial intelligence server 410 may be implemented to be combined together in a single computing system.

Figure 5:
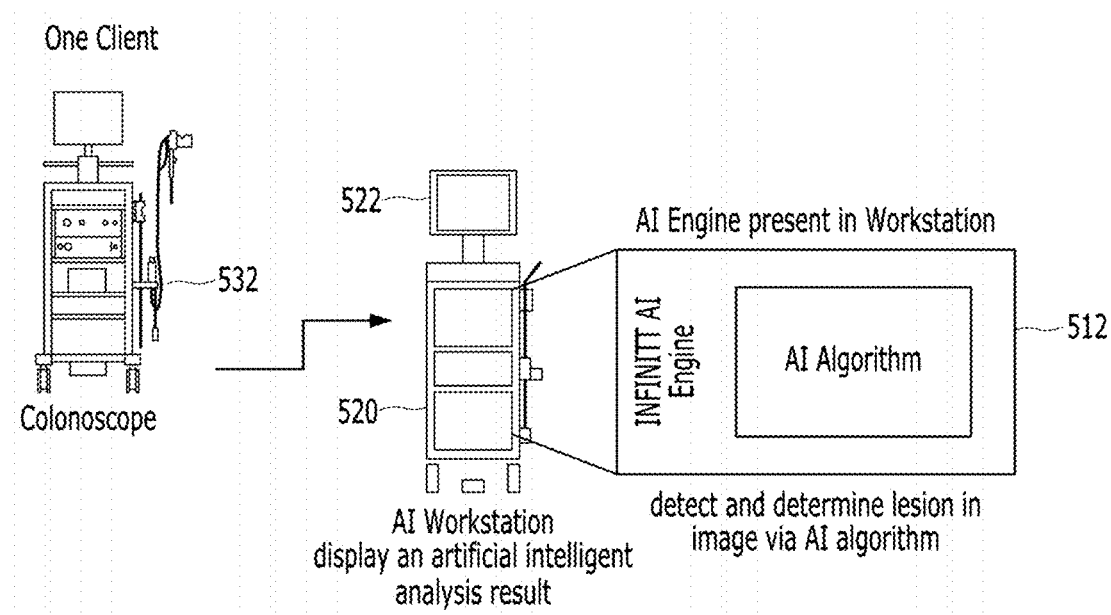
FIG. 5 is a diagram showing a colonoscopic image diagnosis assisting system having a single client structure and peripheral devices according to an embodiment of the present invention.

FIG. 5 is a diagram showing a colonoscopic image diagnosis assisting system having a single client structure and peripheral devices according to an embodiment of the present invention.

A colonoscopic image acquisition module 532 may transfer a colonoscopic image, acquired in real time, to an artificial intelligence workstation 520 in real time, or may transfer a captured image of a colonoscopic image to the artificial intelligence workstation 520.

In this case, the artificial intelligence workstation 520 may include an input/reception interface module (not shown) configured to receive a colonoscopic image (or a captured image) received from the colonoscopic image acquisition module 532.

The artificial intelligence workstation 520 may detect and determine a lesion in a video frame/image by using an artificial intelligence algorithm (a medical image analysis algorithm) 512.

A processor (not shown) in the artificial intelligence workstation 520 may input given image data to the artificial intelligence algorithm 512, may receive the analysis result of the artificial intelligence algorithm 512, and may control a data transfer process between memory or storage (not shown) having the artificial intelligence algorithm 512 stored therein and the processor during the above process.

The output interface module (not shown) of the artificial intelligence workstation 520 may generate the analysis result of the artificial intelligence algorithm 512 as display information, and may transfer the display information to a user display 522. In this case, the transferred information may include whether a finding suspected of being a lesion is detected within a video frame, the coordinates at which the finding suspected of being a lesion is detected, the probability that the finding suspected of being a lesion is a lesion, and the location of the finding suspected of being a lesion in a colorectal or colonoscopic path.

The artificial intelligence workstation 520 may display the analysis result of the artificial intelligence algorithm 512 on a user display 522. In this case, the information displayed on the user display 522 may include whether a finding suspected of being a lesion is detected within a video frame of a currently displayed colonoscopic image, the finding suspected of being a lesion that is visualized to be visually distinguished within the video frame (e.g., the finding suspected of being a lesion that is highlighted, or the finding suspected of being a lesion that is surrounded with a box), the coordinates of the location of the finding suspected of being a lesion within the video frame, and the location of the finding suspected of being a lesion in a colorectal or colonoscopic path.

Figure 6:
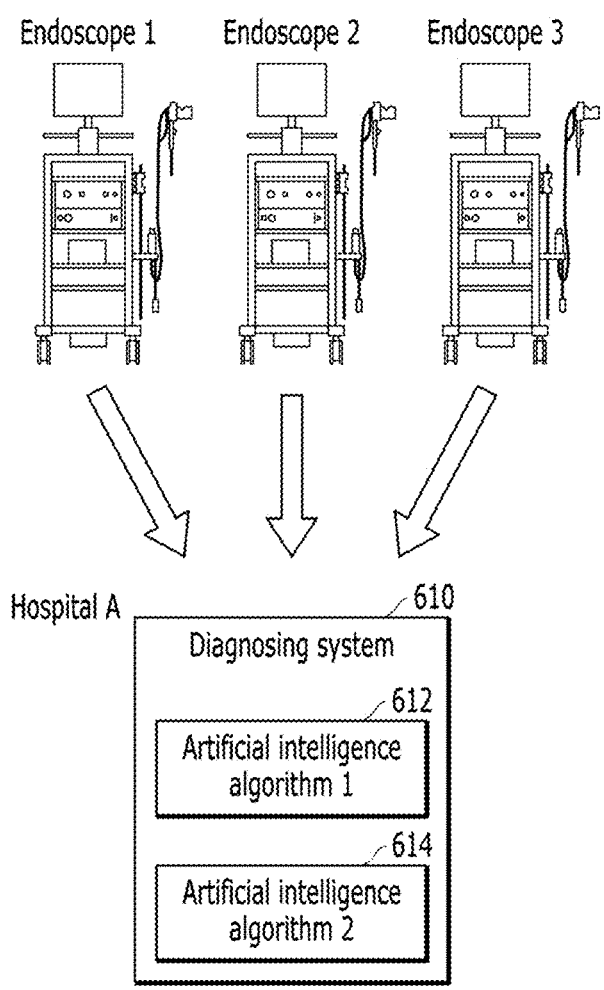
FIG. 6 is a view showing a colonoscopic image diagnosis assisting system and a workflow using the same according to an embodiment of the present invention.

FIG. 6 is a view showing a colonoscopic image diagnosis assisting system and a workflow using the same according to an embodiment of the present invention.

When the diagnosis results and display information of the present invention are used in a hospital, they are displayed by the user system having a user interface capable of displaying auxiliary artificial intelligence diagnosis results after endoscopic data has been received and analyzed, and then the diagnosis results may be verified, the diagnosis results may be replaced, or the acceptance or rejection of the diagnosis results may be determined based on user input.

The processor in a diagnosis assisting system 610 may store the display information in the database with the display information associated with the endoscopic image frame. In this case, the database may be a database inside the diagnosis computing system, and may be stored as medical records for a patient in the future.

The processor may generate external storage data in which the display information and the endoscopic image frame are associated with each other, and may transmit the external storage data to an external database via the transmission module so that the external storage data can be stored in the external database. In this case, the external database may be a PACS database or a database implemented based on a cloud.

In this case, a plurality of medical image diagnosis algorithms 612 and 614 are artificial intelligence algorithms each using an artificial neural network, and the processor may generate evaluation scores based on the respective diagnosis requirements/context-based diagnosis requirements as descriptive information for the plurality of respective medical image diagnosis algorithms.

The diagnosis assisting system 610 of the present invention may internally include the at least two artificial intelligence diagnosis algorithms 612 and 614. Endoscopic image data is transferred from three or more pieces of endoscopy equipment to the diagnosis assisting system 610. The diagnosis assisting system 610 generates diagnosis results by applying the at least two artificial intelligence diagnosis algorithms to each frame of the endoscopic image data. The diagnosis assisting system 610 generates display information by associating the diagnosis results with the frame of the endoscopic image data. In this case, the display information may be generated to include the identification information of a hospital (hospital A) in which the endoscopic image data is generated. Furthermore, the display information may be generated to include the identification information (endoscope 1, endoscope 2, or endoscope 3) given to each piece of endoscope equipment of each hospital.

Figure 7:
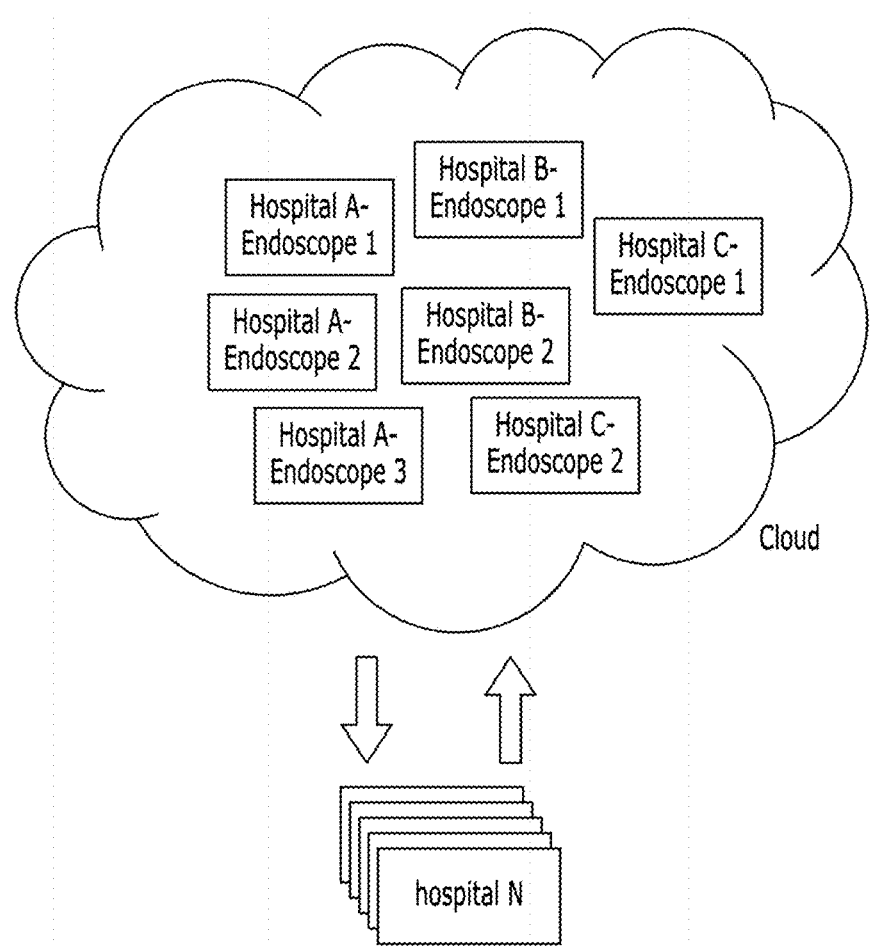
FIG. 7 is a view showing a colonoscopic image diagnosis assisting system and a workflow using the same according to an embodiment of the present invention.

FIG. 7 is a view showing a colonoscopic image diagnosis assisting system and a workflow using the same according to an embodiment of the present invention.

The diagnosis assisting system 610 of FIG. 6 transmits the generated display information to a cloud-based database, and the endoscopic image data and the display information are stored in the cloud-based database in the state in which the endoscopy equipment, in which the endoscopic image data was generated, and the hospital, in which the endoscopic image data was generated, are identified. The display information may be generated by associating diagnosis information with each frame of the endoscopic image data and then stored. The diagnosis information generated for each frame of the endoscopic image data may be automatically generated based on evaluation scores and context-based diagnosis requirements, as described in the embodiments of FIGS. 1 to 5.

When the present invention is applied in a cloud environment, endoscopic image data and diagnosis results may be received by a user system on a hospital side using equipment connected over a wireless communication network, and auxiliary artificial intelligence diagnosis results may be displayed on the user system.

The display information stored in the cloud database may be provided to a hospital designated by a patient, and the patient may receive his or her endoscopic image data and diagnosis information at a hospital that is convenient to access and also receive a doctor's interpretation of diagnosis results and a follow-up diagnosis at the hospital.

In the embodiments of FIGS. 1 to 7, the real-time image acquisition module acquires a real-time endoscopic image from the endoscopic image diagnosis acquisition module/endoscopic equipment. The real-time image acquisition module transmits the real-time endoscopic image to the diagnosis assisting system. The diagnosis assisting system includes at least two artificial intelligence algorithms, and generates display information including diagnosis information by applying the at least two artificial intelligence algorithms to the real-time endoscopic image. The diagnosis assisting system transfers the display information to the user system, and the user system may overlay the display information on the real-time endoscopic image or display the real-time endoscopic image and the display information together.

The real-time endoscopic image may be divided into individual image frames. In this case, the endoscopic image frames may be received by the receiving interface.

The diagnosis assisting system (a computing system) includes the reception interface module, the processor, the transmission interface module, and the memory/storage. The processor includes sub-modules the functions of which are internally implemented by hardware or software. The processor may include a first sub-module configured to extract context-based diagnosis requirements, a second sub-module configured to select artificial intelligence analysis results to be displayed from among diagnosis results generated by applying artificial intelligence diagnosis algorithms to the endoscopic image frame, and a third sub-module configured to generate the display information to be displayed on the screen of the user system.

The plurality of artificial intelligence diagnosis algorithms may be stored in the memory or database (not shown) inside the diagnosis computing system, may be applied to the endoscopic image frame under the control of the processor, and may generate diagnosis results for the endoscopic image frame.

Although a case where the plurality of artificial intelligence diagnosis algorithms is stored in the memory or database (not shown) inside the diagnosis computing system and run under the control of the processor is described in the embodiments of FIGS. 1 to 7, the plurality of artificial intelligence diagnosis algorithms may be stored in memory or a database (not shown) outside the diagnosis computing system according to another embodiment of the present invention. When the plurality of artificial intelligence diagnosis algorithms is stored in the memory or database (not shown) outside the diagnosis computing system, the processor may control the memory or database (not shown) outside the diagnosis computing system via the transmission module so that the plurality of artificial intelligence diagnosis algorithms is applied to the endoscopic image frame and diagnosis results for the endoscopic image frame are generated. In this case, the generated diagnosis results may be transferred to the diagnosis computing system through the receiving interface, and the processor may generate the display information based on the diagnosis results.

The processor extracts diagnosis requirements for the endoscopic image frame by analyzing the endoscopic image frame, which is an image frame of a medical image. The processor selects a plurality of diagnosis application algorithms to be applied to the diagnosis of the endoscopic image frame from among the plurality of medical image diagnosis algorithms based on the diagnosis requirements, and the processor generates the display information including diagnosis results for the endoscopic image frame by applying the plurality of diagnosis application algorithms to the endoscopic image frame. This process is performed on each of the endoscopic image frames by the processor.

The processor may extract context-based diagnosis requirements corresponding to the characteristics of the endoscopic image frame by analyzing the endoscopic image frame. The processor may select a plurality of diagnosis application algorithms to be applied to the diagnosis of the endoscopic image frame based on the context-based diagnosis requirements.

The processor may select a combination of a plurality of diagnosis application algorithms based on the context-based diagnosis requirements. The processor may generate the display information including diagnosis results for the endoscopic image frame by applying the plurality of diagnosis application algorithms to the endoscopic image frame.

The combination of a plurality of diagnosis application algorithms may include a first diagnosis application algorithm configured to be preferentially recommended for the endoscopic image frame based on context-based diagnosis requirements, and a second diagnosis application algorithm configured to be recommended based on a supplemental diagnosis requirement derived from the context substrate diagnosis requirements based on a characteristic of the first diagnosis application algorithm.

The context-based diagnosis requirements may include one or more of a body part of the human body included in the endoscopic image frame, an organ of the human body, a relative location indicated by the endoscopic image frame in the organ of the human body, the probabilities of occurrence of lesions related to the endoscopic image frame, the levels of risk of the lesions related to the endoscopic image frame, the levels of difficulty of identification of the lesions related to the endoscopic image frame, and the types of target lesions.

When an organ to which the endoscopic image frame is directed is specified, for example, when the endoscopic image frame is related to a colonoscopic image, information about whether the image displayed in the current image frame is the beginning, middle, or end of the colonoscopic image may be identified along with the relative location thereof in the colon (the inlet, middle, and end of the organ). In the case of a colonoscopic image, information about whether the image displayed in the current image frame is the beginning (e.g., the esophagus), middle (the inlet of the colon), or end of the colonoscopic image may be identified along with the relative location thereof in a colonoscopic path.

Accordingly, the context-based diagnosis requirements may be extracted based on the types of lesions/diseases that are likely to occur at the identified location and region, the types of lesions/diseases that are likely to be overlooked by medical staff because they are difficult to identify with the naked eye, diagnosis information about lesions/diseases that are not easy to visually identify within the current image frame, and the types of lesions/diseases requiring attention due to their high risk/lethality during a diagnosis among the lesions/diseases that may occur at locations within the organ of the human body to which the current image frame is directed. In this case, the context-based diagnosis requirements may also include information about the types of target lesions/diseases that need to be first considered in relation to the current image frame based on the information described above.

The display information may include the endoscopic image frame, the diagnosis results selectively overlaid on the endoscopic image frame, information about the diagnosis application algorithms having generated the diagnosis results, and evaluation scores for the diagnosis application algorithms.

Although priorities may be allocated to the artificial intelligence diagnosis algorithm in descending order of evaluation scores in the application of diagnoses, there are some additional factors to be taken into consideration.

When a first-priority artificial intelligence algorithm detects a part of the lesions that are likely to occur in connection with the corresponding endoscopic image and a subsequent-priority artificial intelligence algorithm detects an item that is not detected by the first priority algorithm, both the diagnosis results of the first-priority artificial intelligence algorithm and the diagnosis results of the subsequent-priority artificial intelligence algorithm may be displayed together. Furthermore, there may be provided a menu that allows a user to select a final diagnosis application artificial intelligence algorithm based on the above-described criteria. In order to help the user to make a selection, the menu may be displayed together with the diagnosis results of the plurality of AI algorithms and a description of the reason for displaying the diagnosis results.

For example, it is assumed that lesions A1 and A2 are known as being the types of lesions that are most likely to occur within the current image frame and a lesion B is known as being less likely to occur than lesions A1 and A2 and being likely to be overlooked because it is difficult to visually identify. An artificial intelligence diagnosis algorithm X, which has obtained the highest evaluation score for the lesions A1 and A2, may obtain the highest overall evaluation score and be selected as the first diagnosis application algorithm that is preferentially recommended. Meanwhile, there may be a case where the first diagnosis application algorithm obtains the highest evaluation score for the lesions A1 and A2 but obtains an evaluation score less than a reference value for the lesion B. In this case, the lesion B for which the first diagnosis application algorithm exhibits the performance less than the reference value may be designated as a supplemental diagnosis requirement. An artificial intelligence diagnosis algorithm Y that obtains the highest evaluation score for the lesion B, which is a supplemental diagnosis requirement, may be selected as a second diagnosis application algorithm. A combination of the first and second diagnosis application algorithms may be selected such that the combination has high evaluation scores for the reliability and accuracy of the overall diagnostic information, the diagnostic information for a specific lesion/disease is prevented from being overlooked, and the diagnostic performance for a specific lesion/disease is prevented from being poor. Accordingly, logical conditions for the selection of a diagnosis application algorithm may be designed such that an artificial intelligence diagnosis algorithm exhibiting the best performance for the supplemental diagnosis requirement for which the first diagnosis application algorithm is weak, rather than the AI diagnosis algorithm exhibiting a high overall evaluation score, is selected as the second diagnosis application algorithm.

Although the case where the two diagnosis application algorithms are selected has been described as an example in the above embodiment, an embodiment in which three or more diagnosis application algorithms are selected and applied may also be implemented according to the description given herein in the case where the combination of the three or more diagnosis application algorithms exhibits better performance according to the evaluation scores.

The embodiments of FIGS. 1 to 7 are embodiments in which the diagnosis results obtained by the application of the artificial intelligence diagnosis algorithms having high internal evaluation scores are presented and then a user may select the diagnosis results obtained by the application of artificial intelligence diagnosis algorithms having higher evaluation scores. In the embodiment of FIGS. 1 to 7, there is disclosed a configuration conceived for the purpose of rapidly displaying diagnosis results for a real-time endoscopic image. Accordingly, in the embodiment of FIGS. 1 to 7, a combination of artificial intelligence diagnosis algorithms to be displayed for the current image frame is preferentially selected based on context-based diagnosis requirements, the diagnosis results of this combination are generated as display information, and the display information together with the image frame is provided to a user.

In this case, the types of lesions/diseases that are likely to occur in the current image frame, the types of lesions/diseases that are likely to occur in the current image frame and are also likely to be overlooked by medical staff because they are difficult to visually identify, and the types of lesions/diseases requiring attention during diagnosis due to their high risk/lethality among the lesions that may occur in the current image frame may be included in the context-based diagnosis requirements. Furthermore, the types of target lesions/diseases that should not be overlooked in the current image frame based on the types and characteristics of lesions/diseases, and the priorities of the types of target lesions/diseases may be included in the context-based diagnosis requirements.

Diagnosis results are generated using results, to which artificial intelligence algorithms are applied, by the diagnosis computing terminal of the medical staff. In this case, the comments of the medical staff may be added during the process of generating diagnosis results.

In the medical image diagnosis assisting system according to the present invention, the I-scores, i.e., evaluation scores, are transferred from the computing system to the diagnosis computing terminal of the medical staff. Final diagnosis texts may be generated by incorporating the I-scores, i.e., evaluation scores, into the generation of the diagnosis results. According to an embodiment of the present invention, the computing system may generate diagnosis texts together with the I-scores, i.e., evaluation scores, and transfer them to the computing system of the medical staff. In this case, the diagnosis texts generated by the computing system may be written using the diagnosis results based on diagnosis application algorithms having higher I-scores, i.e., higher evaluation scores.

The computing system may provide a user interface configured to allow recommended diagnosis results to be selected using I-scores, i.e., internally calculated evaluation scores, and to allow a radiologist to evaluate/check diagnostic confidence in corresponding recommended diagnoses (e.g., recommended diagnosis algorithms consistent with the diagnosis results of the radiologist) because the evaluation scores are also displayed. The processor of the computing system may select the first and second diagnosis results from among the plurality of diagnosis results as recommended diagnosis results based on the evaluation scores. The processor may generate display information, including the evaluation score for the first diagnosis algorithm, the first diagnosis result, the evaluation score for the second diagnosis algorithm, and the second diagnosis result.

The computing system may generate an evaluation score based on the confidence score of a corresponding diagnosis algorithm, the accuracy score of the diagnosis algorithm, and the evaluation confidence score of a radiologist who provides feedback. The processor may generate the confidence score of each of the plurality of medical image diagnosis algorithms, the accuracy score of the medical image diagnosis algorithm, and the evaluation confidence score of the medical image diagnosis algorithm by the user as sub-evaluation items based on a corresponding one of the plurality of diagnosis results and feedback on the diagnosis result, and may generate an evaluation score based on the sub-evaluation items.

For example, the criteria for the generation of the evaluation score may be implemented as follows:

$$I\text{-score} = a \times (\text{the confidence score of an artificial intelligence algorithm}) + b \times (\text{the accuracy score of the artificial intelligence algorithm}) + c \times (\text{the evaluation confidence score of the artificial intelligence algorithm by a radiologist}) \quad (1)$$

The confidence score of the algorithm may be given to the algorithm by the radiologist. In other words, when it is determined that the first diagnosis result is more accurate than the second diagnosis result, a higher confidence score may be given to the first diagnosis result.

The accuracy score of the algorithm may be determined based on the extent to which the radiologist accepts the diagnosis result of the algorithm without a separate score giving process. For example, in the case where when the first diagnosis result presents ten suspected lesion locations, the radiologist approves nine suspected lesion locations, the accuracy score may be given as 90/100.

Another embodiment in which the accuracy score of the algorithm is given may be a case where an accurate result is revealed through a biopsy or the like. In this case, the accuracy of the diagnosis result of the diagnosis algorithm may be revealed in comparison with the accurate result obtained through the biopsy. When the user inputs the accurate result, obtained through the biopsy, to the computing system, the computing system may calculate the accuracy score of the diagnosis algorithm by comparing the diagnosis result with the accurate result obtained through the biopsy (a reference).

The evaluation confidence score of the radiologist may be provided as a confidence score for the evaluation of the radiologist. In other words, when the radiologist is an expert having a loner experience in a corresponding clinical field, a higher evaluation confidence score may be given accordingly. The evaluation confidence score may be calculated by taking into consideration the years of experience of the radiologist, the specialty of the radiologist, whether or not the radiologist is a medical specialist, and the experience in the corresponding clinical field.

The computing system may update evaluation score calculation criteria according to a predetermined internal schedule while continuously learning the evaluation score calculation criteria by means of an internal artificial intelligence algorithm. The processor may assign weights to the confidence scores of the plurality of respective medical image diagnosis algorithms, the accuracy scores of the plurality of respective medical image diagnosis algorithms, and the evaluation confidence scores of the plurality of respective medical image diagnosis algorithms by the user, which are sub-evaluation items, and may update the weights of the sub-evaluation items so that the weights of the sub-evaluation items can be adjusted according to a target requirement based on the plurality of diagnosis results and feedback on the plurality of diagnosis results by the user.

An example of the target requirement may be a case where adjustment is performed such that there is a correlation between the confidence of the user in the algorithms and the accuracy of the algorithms. For example, first and second diagnosis algorithms having the same accuracy score may have different confidence scores that are given by a radiologist. In this case, when confidence scores are different from each other while exhibiting a certain tendency after the removal of the general errors of the evaluation of the radiologist, it can be recognized that the confidence of the radiologist in the first diagnosis algorithm is different from the confidence of the radiologist in the second diagnosis algorithm. For example, in the case where the first and second diagnosis algorithms generate accurate diagnosis results at nine of a total of ten suspected lesion locations, resulting in an accuracy score of 90/100 but only the first diagnosis algorithm accurately identifies a severe lesion and the second diagnosis algorithm does not identify the lesion, the confidence of the radiologist in the first diagnosis algorithm may be different from the confidence of the radiologist in the second diagnosis algorithm. A means for adjusting the correlation between the accuracy and the confidence may be a means for adjusting the weights of the respective sub-evaluation items or subdividing criteria for the selection of target lesions related to the determination of accuracy. In this case, there may be used a method that classifies lesions according to criteria such as the hardness/severity of an identified lesion, the position of the lesion from the center of a medical image, and the difficulty of identifying the lesion (the difficulty is high in a region where bones, organs, and blood vessels are mixed in a complicated form) and assigns different weights to the diagnosis accuracies of lesions in respective regions.

The computing system may include a function of automatically allocating a plurality of artificial intelligence algorithms that are applicable depending on an image. To determine a plurality of artificial intelligence algorithms applicable to an image, the computing system 100 may classify one examination or at least one image by means of a separate image classification artificial intelligence algorithm inside a recommendation diagnosis system, and may then apply a plurality of artificial intelligence algorithms.

In an embodiment of the present invention, the plurality of medical image diagnosis algorithms may be medical image diagnosis algorithms using artificial neural networks. In this case, the evaluation score and the sub-evaluation items may be generated as descriptive information for each diagnosis algorithm, and the computing system 100 may feed the evaluation score and the sub-evaluation items back to the creator of the diagnosis algorithm so that the information can be used to improve the diagnosis algorithm.

In this case, when each of the artificial neural networks is an artificial neural network using a relevance score and a confidence level, which is being studied recently, a statistical analysis is performed with the evaluation score and the sub-evaluation items associated with the relevance score or confidence level of the artificial neural network, and thus the evaluation score and the sub-evaluation items may affect the improvement of the diagnosis algorithm.

This embodiment of the present invention is designed to provide advantages obtainable by the present invention while minimizing the deformation of the medical image diagnosis sequence of the related art as much as possible.

In another embodiment of the present invention, the computing system may perform the process of generating a plurality of diagnosis results by selecting a plurality of diagnosis application algorithms and then applying the plurality of diagnosis application algorithms to a medical image by itself. In this case, the computing system may transfer not only information about the selected diagnosis application algorithms but also the plurality of diagnosis results based on the diagnosis application algorithms to the diagnosis computing terminal of the medical staff, and the results obtained by applying artificial intelligence algorithms (the diagnosis application algorithms) to the medical image may be displayed on the diagnosis computing terminal of the medical staff.

In this case, an embodiment of the present invention may provide advantages obtainable by present invention even when the computing power of the diagnosis computing terminal of the medical staff is not high, e.g., the diagnosis computing terminal of the medical staff is a mobile device or an old-fashioned computing system. In this case, in an embodiment of the present invention, an agent that applies the artificial intelligence algorithms to the medical image is the computing system, the computing system functions as a type of server, and the diagnosis computing terminal of the medical staff may operate based on a thin-client concept. In this case, in an embodiment of the present invention, the feedback indicators input for the plurality of diagnosis results or the plurality of diagnosis application algorithms via the diagnosis computing terminal of the medical staff by the medical staff may be fed back to the computing system. The feedback indicators may be stored in the memory or database inside the computing system in association with the evaluation targets, i.e., the plurality of diagnosis results or the plurality of diagnosis application algorithms.

As described above, in an embodiment of the present invention, the step of applying the selected algorithms may be performed in the diagnosis system of the clinician, and a plurality of diagnosis results may be transferred to the computing system. In another embodiment of the present invention, the overall step of applying the selected algorithms may be performed within the computing system and then the results of the application may be displayed on the diagnosis system of the clinician.

According to the present invention, work efficiency and diagnostic accuracy may be increased by training on polyps, etc., which may be missed by a user, based on artificial intelligence medical image diagnosis results for each real-time video frame of a colonoscopic image via the artificial intelligence algorithm and then applying the results of the training to the artificial intelligence diagnosis assisting system.

According to the present invention, there is an effect of preventing in advance a situation that may develop into cancer by detecting a lesion or the like at its early stage. Not only lesions of various sizes but also the locations of the lesions in colonoscopic paths are included in labels and used as learning data. Accordingly, according to the present invention, lesion detection rate may be increased by automatically detecting even a considerably small lesion that may easily be missed by a user, and also the locations of lesions in colonoscopic paths may be extracted.

According to the present invention, the incidence of colorectal cancer may be reduced by increasing polyp/lesion detection rate and also eliminating colorectal cancer risk factors in their early stages. Furthermore, the contributions may be made to reducing the causes of colorectal cancer and reducing the frequency of examinations by enabling doctors to find and treat more lesions than before.

According to the present invention, a disease that may easily be missed by a user may be automatically detected during colonoscopy and the location of the disease in a colorectal path (a colonoscopic path) may be presented, so that the user may easily check the disease in real time during colonoscopy and even a report adapted to enable other examiners to check it later may be generated through a simple operation.

According to the present invention, there may be provided the optimized content of artificial intelligence medical image diagnosis results for each real-time image frame of an endoscopic image.

According to the present invention, there may be provided the optimized content of a plurality of artificial intelligence medical image diagnosis results for each real-time image frame.

According to the present invention, there may be provided an optimized combination of a plurality of artificial intelligence medical image diagnosis results as display information for each real-time image frame.

According to the present invention, there may be provided an optimized combination of a plurality of artificial intelligence medical image diagnosis results capable of efficiently displaying diagnosis results that are likely to be acquired, are likely to be overlooked, or have a high level of risk in a current image frame.

According to the present invention, there may be provided the user interface and diagnosis computing system that automatically detect and present diagnosis results that are likely to be acquired, are likely to be overlooked, or have a high level of risk in a current image frame, so that medical staff can check and review the diagnosis results in real time during an endoscopy.

A medical image diagnosis assisting method according to the embodiments of the present invention may be implemented in the form of program instructions, and may be then stored in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A colonoscopic image diagnosis assisting system for assisting diagnosis of a medical image, the colonoscopic image diagnosis assisting system comprising a computing system, wherein the computing system comprises:
   a receiving interface configured to receive a colonoscopic image as the medical image;
   memory or a database configured to store at least one medical image analysis algorithm having a function of analyzing the colonoscopic image;
   a processor; and
   a user display,
   wherein the processor is configured to:
      analyze each video frame of the colonoscopic image using the at least one medical image analysis algorithm;
      detect a finding suspected of being a lesion in the video frame;
      calculate coordinates of a location of the finding suspected of being a lesion; and
      generate display information, including whether the finding suspected of being a lesion is present and the coordinates of the location of the finding suspected of being a lesion,
   wherein the user display is configured to display the finding suspected of being a lesion so that it is visually distinguished in the video frame based on the display information and display the coordinates of the location of the finding suspected of being a lesion so that they are visually associated with the finding suspected of being a lesion,
   wherein the processor is further configured to:
      track a location of the video frame indicative of a current examination region with respect to a colonoscopic path, by using the at least one medical image analysis algorithm;
      calculate the location of the finding suspected of being a lesion in the colonoscopic path based on the location of the video frame in the colonoscopic path and the coordinates of the location of the finding suspected of being a lesion; and generate display information, including whether the finding suspected of being a lesion is present, the coordinates of the location of the finding suspected of being a lesion, and the location of the finding suspected of being a lesion in the colonoscopic path, and wherein the user display is further configured to display the location of the finding suspected of being a lesion in the colonoscopic path so that it is visually associated with the finding suspected of being a lesion based on the display information.

2. The colonoscopic image diagnosis assisting system of claim 1, wherein the processor is further configured to calculate the location of the finding suspected of being a lesion in the colonoscopic path based on a pre-examination medical image including a three-dimensional anatomical structure of a patient to be examined.

3. The colonoscopic image diagnosis assisting system of claim 1, wherein the processor is further configured to extract context-based diagnosis requirements corresponding to characteristics of the video frame in the medical image by analyzing the video frame of the medical image, and wherein the processor is further configured to select a diagnosis application algorithm to perform diagnosis on the video frame from among a plurality of diagnosis application algorithm candidates based on the context-based diagnosis requirements.

4. The colonoscopic image diagnosis assisting system of claim 1, wherein the receiving interface is further configured to receive at least one colonoscopic image from at least one colonoscopic image acquisition module, wherein the processor is further configured to detect a finding suspected of being a lesion for each video frame of the at least one colonoscopic image by using the at least one medical image analysis algorithm, and wherein the processor is further configured to generate display information, including whether the finding suspected of being a lesion is present and the coordinates of the location of the finding suspected of being a lesion, for each video frame of the at least one colonoscopic image.

5. A colonoscopic image diagnosis assisting method, the method being performed by a colonoscopic image diagnosis assisting system including a processor and a user display, the method comprising:

receiving a colonoscopic image;

analyzing, by the processor, each video frame of the colonoscopic image by using at least one medical image analysis algorithm having a function of analyzing the colonoscopic image stored in memory or a database in the colonoscopic image diagnosis assisting system, and detecting, by the processor, a finding suspected of being a lesion in the video frame;

when the finding suspected of being a lesion is present in the video frame, calculating, by the processor, coordinates of a location of the finding suspected of being a lesion;

generating, by the processor, display information, including whether the finding suspected of being a lesion is present and the coordinates of the location of the finding suspected of being a lesion;

when the finding suspected of being a lesion is present in the video frame, displaying, by the user display, the finding suspected of being a lesion so that it is visually distinguished in the video frame based on the display information;

tracking, by the processor, a location of the video frame indicative of a current examination region with respect to a colonoscopic path, by using the at least one medical image analysis algorithm;

calculating, by the processor, a location of the finding suspected of being a lesion in the colonoscopic path; and displaying, by the user display, the coordinates of the location of the finding suspected of being a lesion so that they are visually associated with the finding suspected of being a lesion, wherein the generating comprises generating, by the processor, display information, including whether the finding suspected of being a lesion is present, the coordinates of the location of the finding suspected of being a lesion, and the location of the finding suspected of being a lesion in the colonoscopic path, and wherein the displaying the coordinates of the location of the finding suspected of being a lesion comprises displaying, by the user display, the location of the finding suspected of being a lesion in the colonoscopic path so that it is visually associated with the finding suspected of being a lesion based on the display information.

6. The colonoscopic image diagnosis assisting method of claim 5, wherein the receiving comprises receiving at least one colonoscopic image from at least one colonoscopic image acquisition module, wherein the detecting comprises detecting whether a finding suspected of being a lesion is present for each video frame of the at least one colonoscopic image by using the at least one medical image analysis algorithm, and wherein the generating comprises generating display information, including whether the finding suspected of being a lesion is present and the coordinates of the location of the finding suspected of being a lesion, for each video frame of the at least one colonoscopic image.

* * * * *